United States Patent
Teoh et al.

(10) Patent No.: US 9,737,252 B2
(45) Date of Patent: Aug. 22, 2017

(54) VASCULAR ACCESS BLOOD COLLECTION DEVICES AND RELATED METHODS

(71) Applicant: B. BRAUN MELSUNGEN AG, Melsungen (DE)

(72) Inventors: Hui Kuun Teoh, Penang (MY); Wen Jenn Lim, Penang (MY); Teng Sun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 138 days.

(21) Appl. No.: 14/576,802

(22) Filed: Dec. 19, 2014

(65) Prior Publication Data

US 2015/0173663 A1   Jun. 25, 2015

Related U.S. Application Data

(60) Provisional application No. 61/918,951, filed on Dec. 20, 2013.

(51) Int. Cl.
| | | |
|---|---|---|
| *A61B 5/153* | (2006.01) | |
| *A61M 39/10* | (2006.01) | |
| *A61B 5/15* | (2006.01) | |
| *A61M 25/06* | (2006.01) | |

(52) U.S. Cl.
CPC ........ *A61B 5/1535* (2013.01); *A61B 5/15003* (2013.01); *A61B 5/150213* (2013.01); *A61B 5/150221* (2013.01); *A61B 5/150259* (2013.01); *A61B 5/150274* (2013.01); *A61B 5/150389* (2013.01); *A61B 5/150503* (2013.01); *A61B 5/150992* (2013.01); *A61M 25/0618* (2013.01); *Y10T 29/49826* (2015.01)

(58) Field of Classification Search
CPC ........................ A61M 5/3293; A61B 5/1405
See application file for complete search history.

(56) References Cited

U.S. PATENT DOCUMENTS

| | | | |
|---|---|---|---|
| 2011/0009717 A1* | 1/2011 | Davis ................... | A61B 5/1405 600/309 |
| 2012/0016266 A1* | 1/2012 | Burkholz ............. | A61B 5/1405 600/581 |
| 2015/0173660 A1* | 6/2015 | Choon Meng ....... | A61B 5/1405 600/583 |

OTHER PUBLICATIONS

Technical Manual, "B. Braun Introcan Safety® IV Catheter." (2009): 1-4.*

* cited by examiner

*Primary Examiner* — Michael C Stout
*Assistant Examiner* — Nicholas E Kolderman
(74) *Attorney, Agent, or Firm* — Klein, O'Neill & Singh, LLP

(57) ABSTRACT

The present disclosure is directed to a needle assembly for drawing blood. The needle assembly can be a standalone or part of an over-the-needle medical device, such as an intravenous catheter. A blood collection device is attached directly or indirectly to the needle hub of the needle assembly and/or to a catheter hub, such as through a Y-site or adaptor connected to a tubing that is connected to the catheter hub. The needle is configured to access the vascular system to draw blood, which then passes to the blood collection device via the needle lumen, which has a tip having a discontinuity opening, an opening with a movable stem, or a shaft element with a lumen.

14 Claims, 11 Drawing Sheets

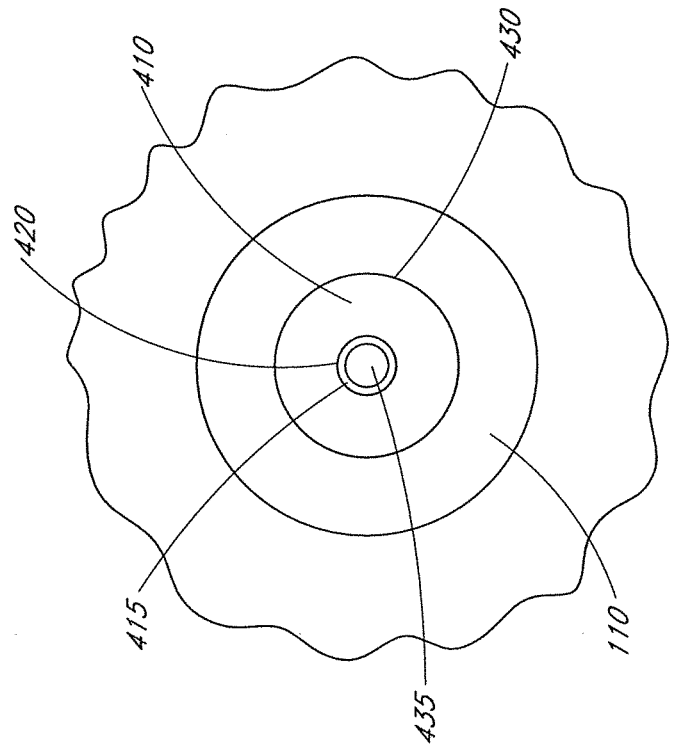
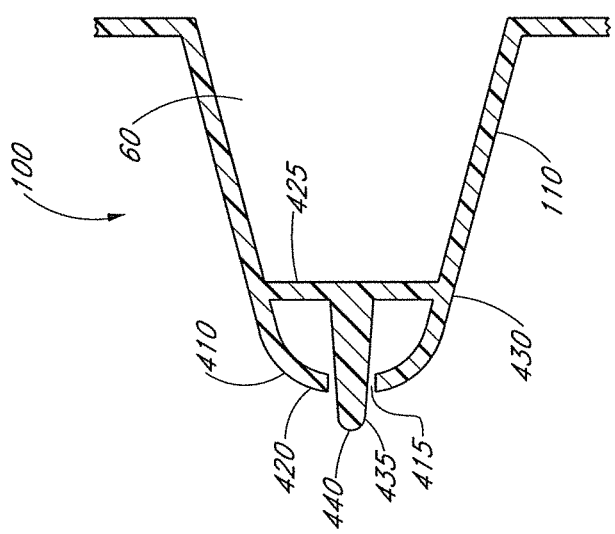
FIG. 5B
FIG. 5A

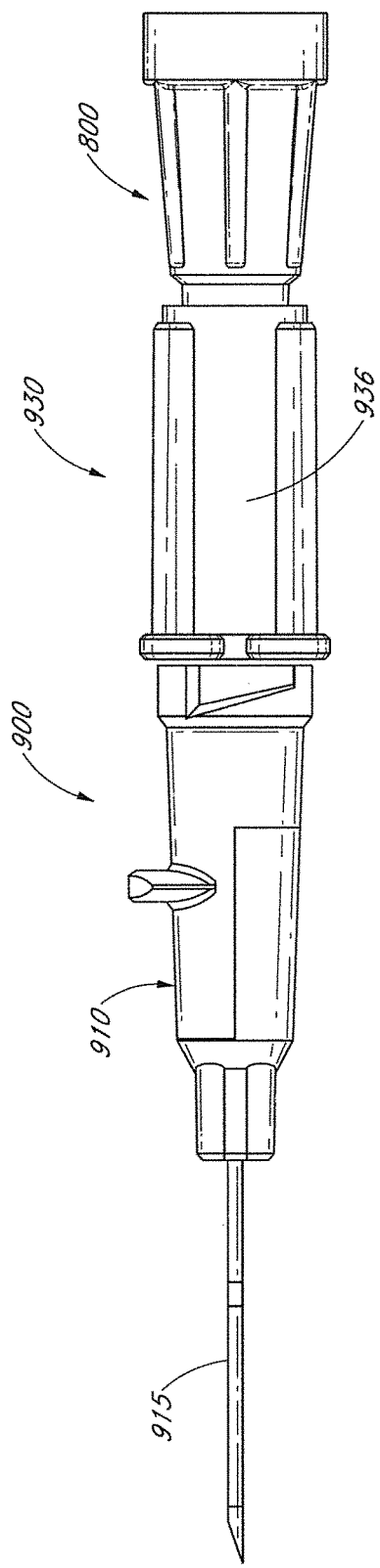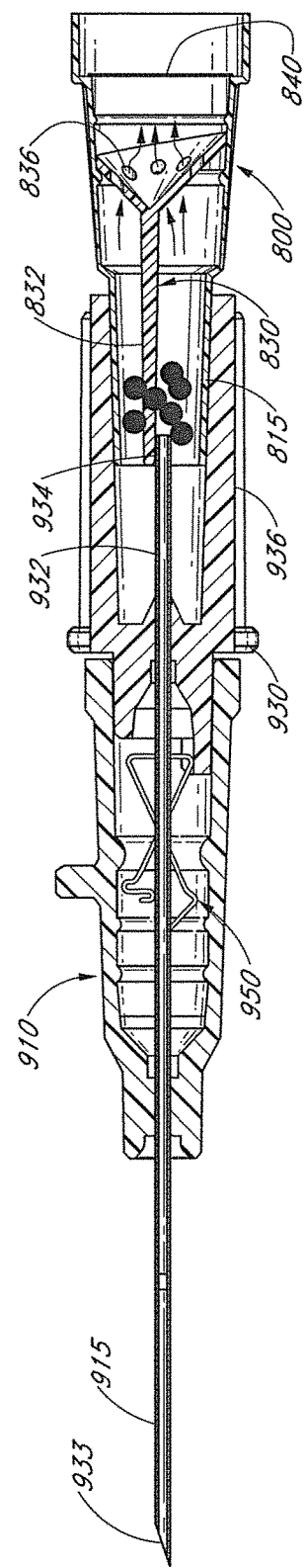
*FIG. 8E*
*FIG. 8F*

VASCULAR ACCESS BLOOD COLLECTION DEVICES AND RELATED METHODS

FIELD OF ART

The disclosure relates generally to vascular access devices having blood collection capabilities for use where blood is withdrawn from a patient. More specifically, different sampling tip configurations are disclosed for use with medical devices to facilitate dispensing of biological samples.

BACKGROUND

Blood sampling is a common health care procedure involving the withdrawal of a useable quantity of blood from a patient. Blood samples are commonly taken from hospitalized, homecare, and emergency room patients either by finger stick, heel stick, or venipuncture. Once collected, blood samples are analyzed via one or more blood test levels.

Blood tests determine the physiological and biochemical states of the patient, such as disease, mineral content, drug effectiveness, and organ function. Blood tests may be performed in a laboratory, a distance away from the location of the patient, or performed at the point of care, near the location of the patient. One example of point of care blood testing is the routine testing of a patient's blood glucose levels, which involves the extraction of blood via a finger stick and the mechanical collection of blood into a diagnostic cartridge. Thereafter the diagnostic cartridge analyzes the blood sample and provides the clinician a reading of the patient's blood glucose level. Other devices are available which analyze blood gas electrolyte levels, lithium levels, ionized calcium levels. Furthermore, some point of care devices identify markers for acute coronary syndrome (ACS) and deep vein thrombosis/pulmonary embolism (DVT/PE).

Despite the rapid advancement in point of care testing and diagnostics, blood sampling techniques have remained relatively unchanged. Blood samples are frequently drawn using hypodermic needles, or vacuum tubes coupled to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Furthermore, each device adds time and cost to the testing process.

SUMMARY

The various embodiments of a blood collection device have several features, no single one of which is solely responsible for their desirable attributes. Without limiting the scope of the present embodiments as set forth in the claims that follow, their more prominent features now will be discussed briefly.

Aspects of the present disclosure include a needle assembly that comprises a hub comprising an opening and an interior cavity, a blood collection device connected to the hub and comprising a conically shaped tip extending from a body comprising a wall and defining an interior cavity to store blood, and a gas permeable vent disposed on the wall. The tip can project into the opening and into the interior cavity of the hub to receive blood flashback and has an opening comprising a lip extension, a slanted end surface, crenulations, an oculus, or a movable stem.

The hub can be a needle hub having a needle with a needle tip. The crenulations may comprise a plurality of evenly spaced projections.

The tip can be a Luer tip. The needle assembly can further comprise a catheter hub with a catheter tube in which the needle extends through the catheter tube. In some examples, instead of a Luer tip or a Luer connection between the blood collection device and the hub to which the blood collection device is connected to for receiving blood samples, such as a cannula hub or a catheter hub, the fitting between the two components can be any number of customized fitting connection provided a sufficient seal is produced so that no blood leakage or exposure or minimal blood leakage or exposure can be expected.

A needle guard can be positioned inside an interior cavity of the catheter hub.

The needle can define a lengthwise axis and the movable stem can be located off the lengthwise axis. The movable stem can be connected to a non-symmetrical activator having an apex.

Another aspect of the present disclosure includes a method for manufacturing a needle assembly that comprises forming a hub comprising an opening and an interior cavity, forming a blood collection device comprising a conically shaped tip extending from a body comprising a wall and defining an interior cavity with a storage capacity, and a gas permeable vent disposed on the wall, and projecting the tip into the opening and into the interior cavity of the hub so that the interior cavity of the hub and the interior cavity of the blood collection device are in fluid communication. The tip can have an opening comprising a lip extension, a slanted end surface, crenulations, an oculus, or a movable stem.

The method can further comprise attaching a needle to a distal end of the hub and projecting a proximal end of the needle into the interior cavity of the hub so that the tip of the blood collection device surrounds the proximal end of the needle.

The method can further comprise attaching a needle to a distal end of the hub and projecting the needle in through a catheter hub and a catheter tube.

The method can further comprise placing a needle guard comprising inside an interior cavity of the catheter hub.

The method can further comprise an activator having an apex and the movable stem attached to the activator at the apex.

The body of the blood collection device can be made from a compressible plastic material.

The method can further comprise a valve and a valve opener located inside the interior cavity of the catheter hub.

Yet another aspect of the present disclosure includes a cannula device that comprises a needle hub comprising a first needle having a distal end and a proximal end, said distal end extending distal of a distal end of the needle hub and said proximal end provided in an interior of the needle hub, and a blood collection device comprising a tip having an opening and extending from a body, and attached to the needle hub. The tip can be coupled to the proximal end of the needle and are in fluid communication.

The tip can be sized to fit over the proximal end of the needle or within a lumen of the needle. The tip can be coupled to the proximal end of the needle with an elastomeric coupler.

The cannula device can further comprise a septum at a proximal end of the needle hub forming a seal around the tip of the blood collection device.

The cannula device can further comprise a vent plug attached to a proximal end of the body of the blood collection device. A gas vent can be formed in the body of the blood collection device.

Still yet another aspect of the present disclosure includes a blood collection device that comprises a conically shaped tip extending from a housing having a wall and defining an interior, a dome on a distal end of the conically shaped tip comprising an oculus defining a leading edge, and a pin extending distally from the cross piece and through the center of the oculus. The pin can extend distally past the leading edge.

The blood collection device can further comprise a cross piece across a diameter of a circle defined by a base of the dome, wherein the pin extends from the cross piece. The cross piece can be a single elongated rectangular strip. The cross piece can be a round plate with openings to permit fluid flow through. The pin can extend from internal wall surfaces of the tip.

Another aspect of the present disclosure includes a blood collection device that comprises a body defining an interior cavity configured to retain a fluid, a tip coupled to the body, and a gas permeable filter at a proximal end of the body. The body can be compressible to cause the tip to move distally.

The tip is an actuator comprising a distal member and an activator coupled to the proximal end of the distal member. The activator can be secured to the interior cavity of the body and define a plurality of diffuser holes.

The distal member is offset from a central axis of the compressible body. A plurality of protruding rings can be formed in the interior cavity of the body to secure the activator.

The blood collection device can further comprise a cap secured to the proximal end of the body.

An aspect of the present disclosure includes a method for testing blood that includes providing a needle connected to a hub element, providing a blood collection device in fluid communication with the needle comprising a nozzle sized and shaped to form a droplet, inserting the needle into a patient to cause blood flow, collecting blood in the blood collection device, separating the blood collection device from the hub element and dispensing blood from the blood collection device using a marker-type stroke.

The blood collection device can have a conically shaped tip having a distal opening. The distal opening may not have a continuous round inside circumference.

The blood collection device can have a body defining an interior cavity configured to retain a fluid, a tip coupled to the body, and a gas permeable filter at a proximal end of the body, the body being compressible to cause the tip to move distally.

The blood collection device can further comprise a conically shaped tip extending from a housing having a wall and defining an interior, a dome on a distal end of the conically shaped tip comprising an oculus defining a leading edge, and a pin extending distally from the cross piece and through the center of the oculus, with the pin extending distally past the leading edge.

Blood sampling test strips can also be inserted in the space at 814 in the blood sampling device. The test strip could first be coiled smaller, and inserted into the blood sampling device through the luer opening. The test strip will then uncoil when it is in space 814. This test strip can provide the basic blood information (blood type, glucose level, oxygen level of the patient). For additional testing, the clinician can use the blood accumulated in the blood sampling device. This will quicken the whole process of blood sampling and/or testing in an emergency situation. Alternatively the test strip can be sized to fit in the blood sampling device.

BRIEF DESCRIPTION OF THE DRAWINGS

These and other features and advantages of the present devices, systems, and methods will become appreciated as the same becomes better understood with reference to the specification, claims and appended drawings wherein:

FIG. 5A shows another embodiment of a blood collection device having a connector tip in a side cross section view.

FIG. 5B shows a front view of the embodiment of FIG. 5A.

FIG. 8E shows one embodiment of a catheter assembly including the blood collection device of FIG. 8A.

FIG. 8F shows a cross-sectional view of the catheter assembly of FIG. 8E with the blood collection device of FIG. 8B.

DETAILED DESCRIPTION

The detailed description set forth below in connection with the appended drawings is intended as a description of the presently preferred embodiments of blood collection devices provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
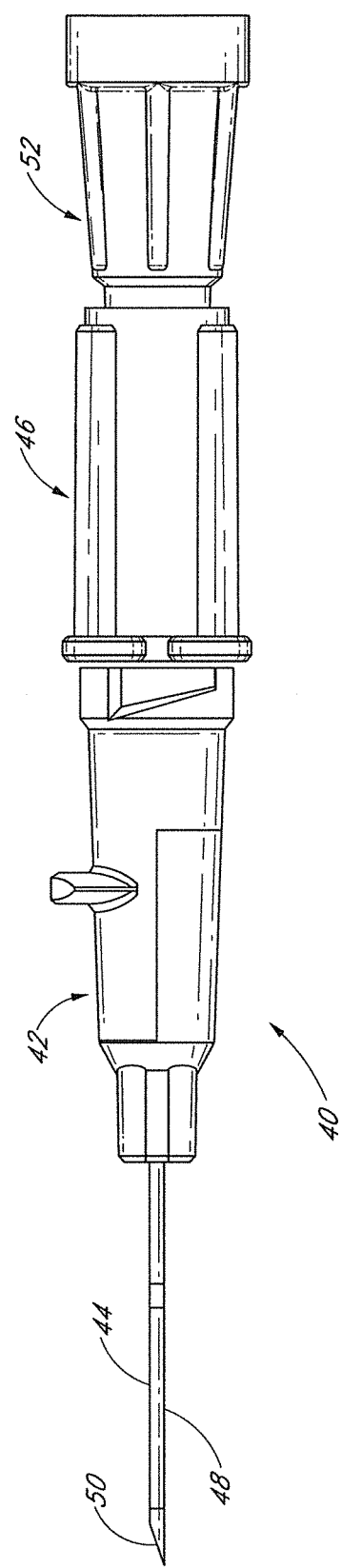
FIG. 1 is a schematic side view of a needle assembly having a blood collection device.

FIG. 1 is a schematic side view of an over-the-needle catheter assembly 40 provided in accordance with aspects of the present disclosure, which comprises a catheter hub 42 with a catheter tube 44 and a needle hub 46 with a needle tube 48 extending distally thereof and through the catheter tube 44 so that the needle tip 50 extends distally of a distal opening of the catheter tube. Also shown is a blood collection device 52 located on the proximal end of the needle hub 46. The catheter assembly 40 may include a needle guard for blocking the needle tip following successful venipuncture, a valve for blocking blood flow, such as blood flashback, and optionally with a valve opener for opening the valve. In some examples, a valve is incorporated that opens without a valve opener, such as by fluid pressure only. These components may be located inside the catheter hub or outside of the catheter hub. In an example, the blood collection device 52 engages the needle hub 46 in a Luer slip and may be used with any number of prior art needle hubs. In other examples, the blood collection device 52 may engage the needle hub 46 in a Luer lock.

Figure 2B:
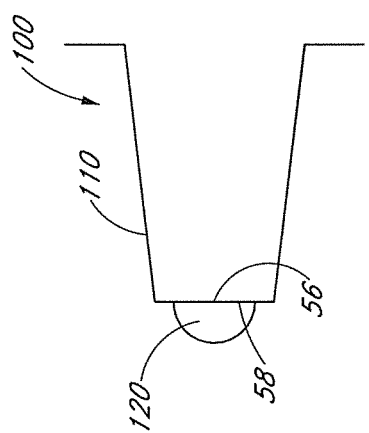
FIG. 2B shows the embodiment of FIG. 2A in a top view.
Figure 2A:
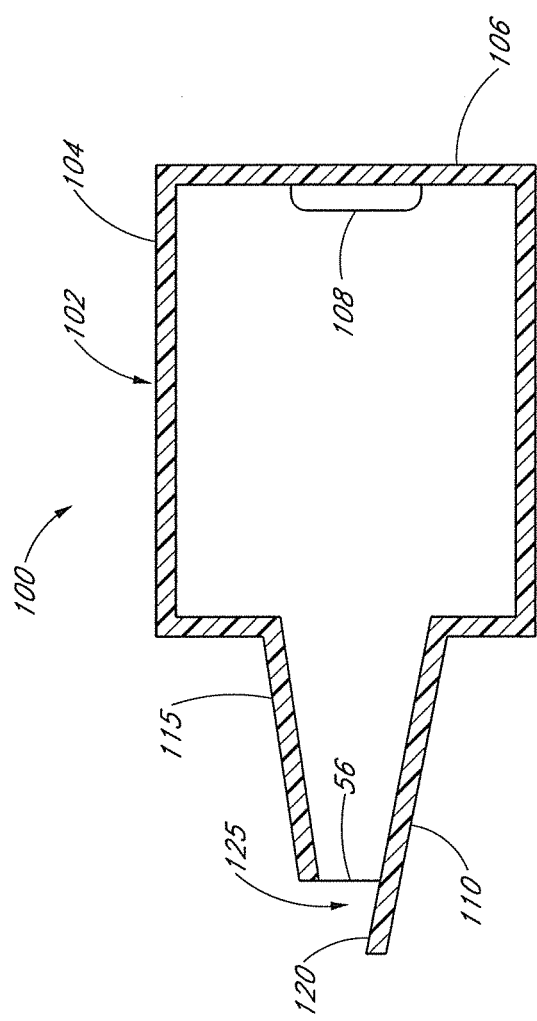
FIG. 2A shows one embodiment of a blood collection device having a connector tip in a side cross section view.

FIG. 2A shows an exemplary blood collection device 100 provided in accordance with aspects of the present disclosure, which may be used with a catheter assembly, a needle hub, or any number of prior art medical devices with fluid flow, such as with blood flashback. As shown, the device 100 has a body 102 with a generally conical tip 110. In one embodiment, the tip 110 is a Luer tip in which a continuous wall 115 of the tip 110 is formed according to current or future ISO standards for medical fittings. A lip extension 120 extends from the opening 56 of the tip 110 and beyond the distal end edge 58 to create a "shovel" shaped section, which may be referred to as an opening with a discontinuity or a discontinuity opening 125, such that the perimeter defining the opening is not round.

The body 102 has a wall structure 104 with a generally cylindrical configuration with other shapes contemplated. The body may be made from a pliable plastic material so that it can be squeezed and compressed by a user. A gas permeable vent 108 is disposed on the proximal end wall 106 of the body 102 to permit venting. For example, when the tip 110 of the blood collection device 100 is disposed in an extravascular system (not shown), such as to a catheter hub, a needle hub, or in a port of a Y adaptor that is attached to a catheter hub via a tubing, and blood is allowed to flow into the body 102 by venting air or gas out the gas permeable vent 108, which is liquid impermeable, such as a hydrophobic filter. In other embodiments, the gas vent 108 is located elsewhere on the wall structure 104 with the location at a high point on the body 102 being more preferred. As further discussed below, the discontinuity opening 125 allows a blood droplet to form with a lower surface tension compared to one formed with a round opening. This in turn allows the droplet to easily drip or be dispensed from the tip 110 to facilitate testing. Thus, an aspect of the present device and method is understood to include a Luer tip extending from a body section having an enclosed space with at least one vent having a gas vent filter, such as a hydrophobic filter, located thereon or thereover, and wherein the Luer tip has an opening with a discontinuity for lowering surface tension of a droplet formed at the opening. The droplet can be a biological sample, such as a blood droplet.

The blood collection device 100 resembles a pipette or a dropper with one notable exception. Whereas a dropper and a pipette are designed to be squeezed to release a quantity of fluid, the present blood collection device 100 utilizes a unique tip in combination with gravity to form an easily releasable droplet at the tip 110, which can then be used for further testing, such as with a glucose test strip. No squeezing is required, although it is possible to squeeze the body to facilitate dripping of blood droplets.

As shown in FIG. 2B, which is a partial top view of the device 100 of FIG. 1, the lip extension 120 at the discontinuity opening 125 is rounded and curves back to the remainder of the tip 110. This configuration allows the connector tip 100 to break the surface tension of the blood being sampled, leading to improved flow and eliminating the need for a user to shake the device in an attempt to break the surface tension. In some examples, the distal end edge 58 may be shaped, such as with protrusions and angular surfaces, to break up cohesive forces between liquid molecules that tend to improve surface tension. In some examples, instead of a Luer tip or a Luer connection between the blood collection device and the hub to which the blood collection device is connected to for receiving blood samples, such as a cannula hub or a catheter hub, the fitting between the two components can be any number of customized fitting connection provided a sufficient seal is produced so that no blood leakage or exposure or minimal blood leakage or exposure can be expected.

For other needle assemblies, catheter assemblies, and blood collection devices and their components disclosed herein below, such as for other blood collection devices having different tip fitting feature or surface tension reduction feature, it is understood that where a feature is shown in the subsequent drawings but not expressly described and is otherwise the same or similar to the feature or features described elsewhere, such as above with reference to the blood collection device of FIGS. 2A and 2B, the disclosed part or parts shown in the subsequent drawing figures but not expressly described, because of redundancy or because knowledge is understood to be built on a foundation laid out by the earlier disclosures, may nonetheless be understood to be described or taught by the same or similar features expressly set forth herein in which the feature or features have been described. Said differently, subsequent disclosures of the present application are built upon the foundation of earlier disclosures and incorporate the teachings of earlier disclosures unless the context indicates otherwise. The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following needle assemblies and blood collection devices incorporate the teachings of earlier embodiments unless the context indicates otherwise. Therefore, it is contemplated that later disclosed embodiments enjoy the benefit of earlier expressly described embodiments unless the context indicates otherwise.

Figure 3B:
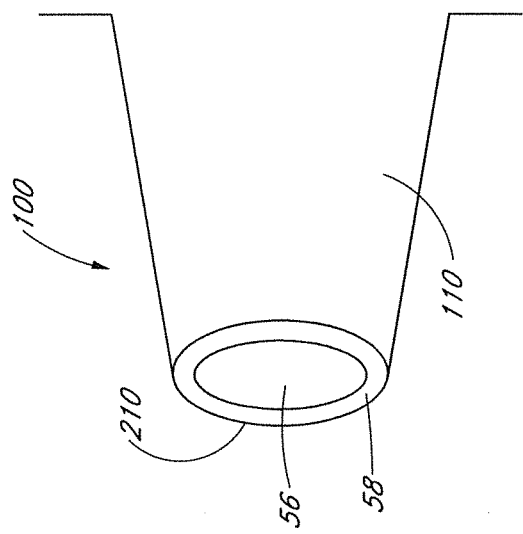
FIG. 3B shows the embodiment of FIG. 3A in a top view.
Figure 3A:
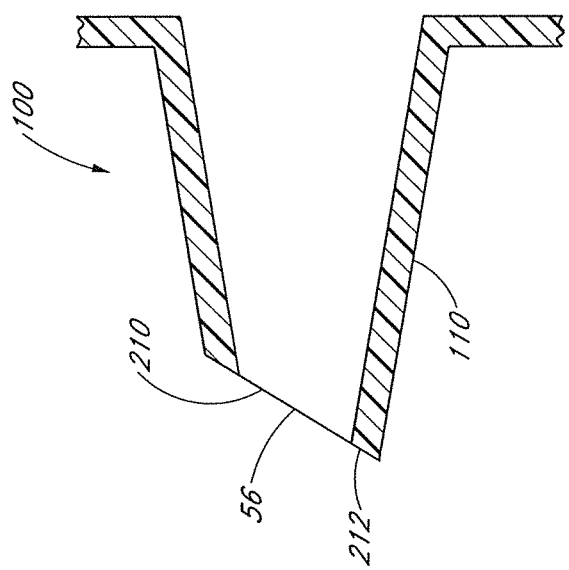
FIG. 3A shows another embodiment of a blood collection device having a connector tip in a side cross section view.

FIG. 3A is a cross-sectional side view and FIG. 3B is a top view of a tip 110 of another blood collection device 100 in accordance with further aspects of the present disclosure, shown without a body 102. In the present embodiment, the end of the tip 110 has a slanted terminal end defining a slanted surface tip 210. In other embodiments, multiple distinct slanted surfaces may be provided at the opening 56 to have more than a single slope or single slant at the distal end edge 58. The leading edge 212 of the slanted surface tip 210 is a single, smooth continuous loop but is not perpendicular to the longitudinal axis of the device 100. In other embodiments, the leading edge is not smooth, such as having bumps or fins. Looking directly at the leading edge 212, an oval shaped is provided by the slanted surface 210, which again forms an opening that is not round. The leading edge 212 helps to break the surface tension of the blood, as only a portion of the leading edge contacts the blood initially.

Figure 4:
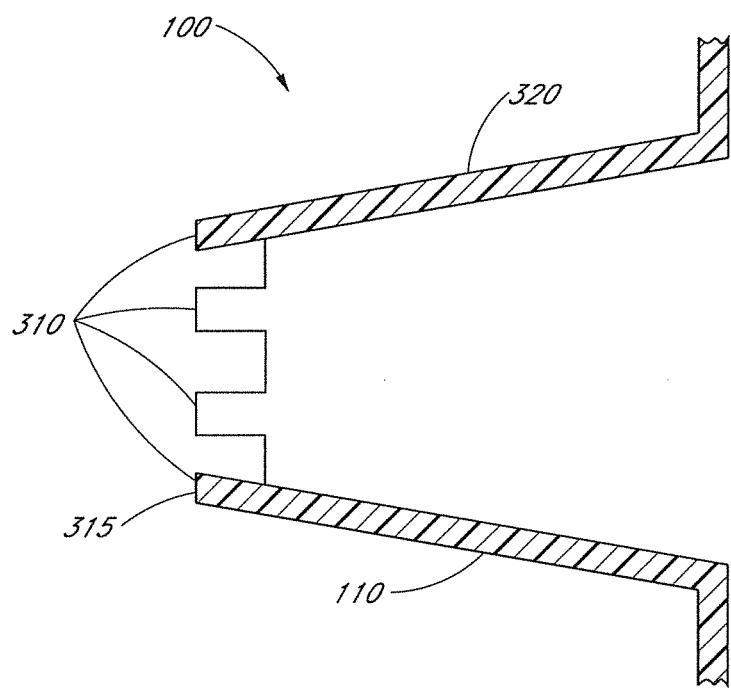
FIG. 4 shows another embodiment of a blood collection device having a connector tip in a side cross section view.

FIG. 4 shows another embodiment of a blood collection device 100 having a tip 110 with crenulations 310 or "tooth" shaped projections around a leading edge 315 of the tip 110, shown without a body 102. When compared to a typical Luer tip with a round end opening, in the illustrated embodiment, the blood collection device 100 has material removed from the wall 320 in alternating sections around the tip 110 of the blood collection device 100. In one embodiment, the areas of removed material are equal to the alternating remaining sections of material, both in width and depth. In another embodiment, the crenulations 310 have substantially the same height and width meaning that each protrusion of the crenulations 310 have substantially the same height and width and can be evenly spaced or irregularly spaced. In this way, as with other embodiments, only a portion of the leading edge comes in contact with blood present at the tip, breaking the surface tension of the blood and causing it to flow more freely. In another embodiment, the crenulations 310 are not symmetrical or evenly spaced yet still allow for improved flow due to the lowering of surface tension. In other embodiments, the crenulations 310 have two or more different sizes, such as different widths and/or different heights.

With reference now to FIGS. 5A and 5B, another embodiment of a blood collection device 100 having a tip 110 with a dome shaped end 410 and an oculus 415 on the leading edge 420 of the tip 110 is shown without a body 102. In one embodiment, more than one oculus 415 is provided. In addition, the embodiment includes an internal cross piece 425 located near the base 430 of the dome shaped end 410, in the lumen 60 of the tip 110. The cross piece 425 forms a chord across the diameter of the base 430 of the dome shaped end 410. Extending distally through the oculus 415 of the dome shaped end 410 from the center of the cross piece 425 is a pin or post 435. The cross piece 425 may be a single elongated rectangular strip, multiple strips, or a round plate with openings to permit fluid such as blood to flow through. The pin or post 435 is generally cylindrical with a hemispherical tip 440. The hemispherical tip 440 extends distally past the leading edge 420 of the dome shaped end 410. The pin 435 and the hemispherical tip 440 are configured to break the surface tension of blood thereby causing the blood to flow more freely through the oculus 415. In another embodiment, the cross piece 425 is not unitarily formed with the tip 110. In other embodiments, the pin 435 or post extends from the internal wall surfaces of the tip 110 but not from the cross piece 425.

Figure 6:
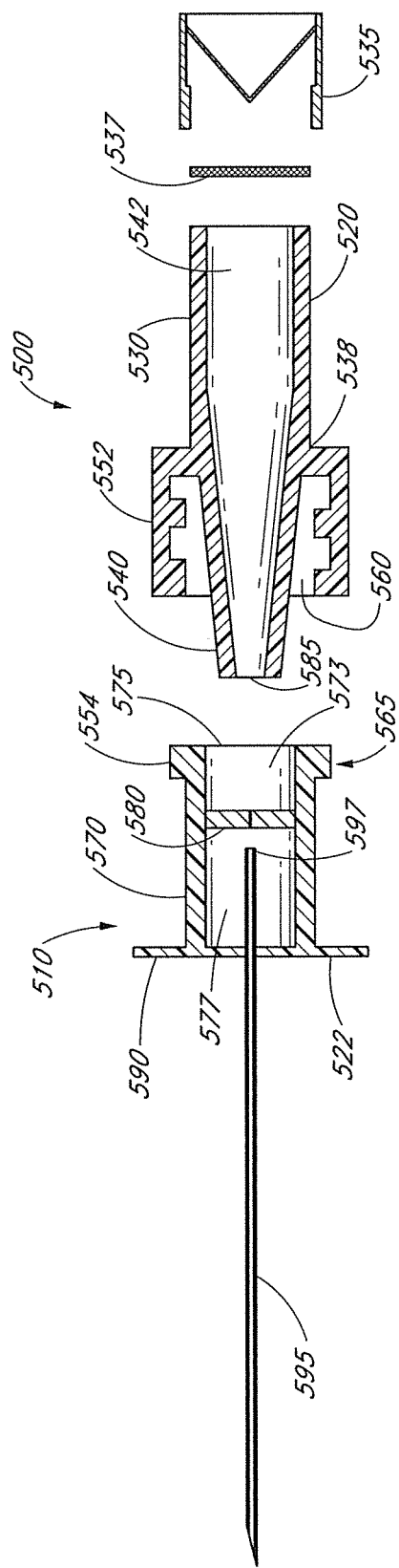
FIG. 6 shows an exploded side cross section view of needle assembly and a blood collection device having a connector tip.

FIG. 6 shows a needle assembly 498 comprising a needle hub 510 with a needle 595 and a blood collection device 500 provided in accordance to further aspects of the present devices, systems, and methods. The blood collection device 500 of the present embodiment is configured to couple to the needle hub 510, which has a needle 595 that is useable with a vascular access device, such as a catheter with a catheter tube. In one embodiment, the blood collection device 500 is configured for use with any hub, with or without a needle, for example a catheter hub.

As shown, the blood collection device 500 includes a body 520, which comprises a hollow elongated portion 530, and a tip 540, which may be formed with a Luer taper. At the proximal end of the blood collection device 500, a cap 535 is provided for retaining a gas permeable vent 537, such as a hydrophobic filter. In other examples, the gas permeable vent 537 is simply wedged into an annular void or a rim formed at the proximal end of the body 520 without using a separate cap 535. The cap 535 may optionally include a pin or a needle to form, such as to puncture, a hole through the gas permeable vent 537 to facilitate smoother flow. The gas permeable vent 537 may also be peelable from the cap 535 or from the cylindrical portion 530.

At the transition 538 between the cylindrical portion 530 and the tip 540, which may be a Luer tip with a taper, a collar 552 is provided with internal threads 560, which together with the tip 540 may be referred to as a male threaded Luer. The threaded collar 552 is configured to engage external threads 554 on the proximal end 565 of the needle hub 510. In one example, the tip 540 is a Luer tip without the threaded collar 552. Thus, aspects of the present disclosure include a blood collection device having a male threaded Luer.

The hollow body portion 570 of the needle hub 510 defines an interior 575 having a female Luer taper at a proximal opening 573 and a septum 580 located inside the interior. In some examples, the septum 580 is omitted. In other examples, the proximal opening 573 is not a standard Luer. The opening 573 is sized and shaped to receive the tip 540 of the blood collection device 500 and to permit the septum 580 to expand or deflect when the tip projects therethrough. When the tip 540 is inserted into the opening 573, the tip opens the slits (not shown) on the septum 580. Thus, when the blood collection device 500 is coupled to the needle hub 510 and the tip 540 opens the septum 580, fluid communication is provided between the needle lumen of the needle 595 and the interior cavity 542 of the blood collection device 500. On the distal end 522 of the hollow body portion 570 of the needle hub 510 is a distal end wall 590, which may embody any number of size and shape for use with various vascular devices, such as to couple to any known prior art catheter hubs, adaptors, valves, Y-adaptors, etc. In one embodiment, the open distal end 585 of the Luer tip 540 is inserted into the interior 575 of the needle hub 510 a sufficient amount or distance to surround or project over the proximal end 597 of the needle 595. This allows for primary blood flashback from the needle lumen to flow directly into the blood collection device 500. In some examples, the open distal tip 585 of the blood collection device forms a close fit over the proximal end 597 of the needle 595. In another embodiment, there is a small gap between the needle exterior surface at the proximal end 597 and the interior diameter of the open distal tip 585.

As shown, the needle assembly 498 of FIG. 6 is understood to include a needle 595 for accessing the vascular system, which draws blood through the needle lumen and into the interior cavity 542 of the blood collection device 500. The blood collection device 500 can then be disconnected from the needle hub 510. Once removed, the slit of the septum 580 inside the needle hub closes and forms a seal to prevent blood leakage out through the proximal opening of the needle hub 510. Blood is therefore retained in the distal chamber 577 of the needle hub 510, between the distal end wall 590 and the septum 580. Thus, an aspect of the present disclosure is understood to include a needle attached to a needle hub and wherein said needle hub comprises a body defining an interior cavity having a septum located therein. As disclosed, said septum has at least one slit for sealing against a tip of a blood collection device, which tip may comprise a Luer taper.

The blood collection device 500 may be used to dispense blood samples captured therein for any number of tests. In one example, the elongated body 530 of the blood collection device 500 is made from a pliable material to permit squeezing, which forces blood samples out the open distal tip 585. In other embodiments, the open distal tip 585 has a discontinuity opening or other surface tension reducing features to facilitate dispensing of blood droplet or droplets from the opening of the tip, which can be one of the openings disclosed in FIGS. 2A-5B.

Figure 7A:
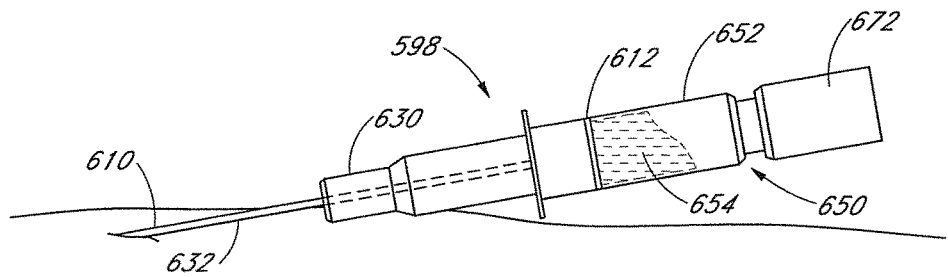
FIGS. 7A-7C show a side view of another embodiment of a vascular access device with a blood collection device.
Figure 7B:
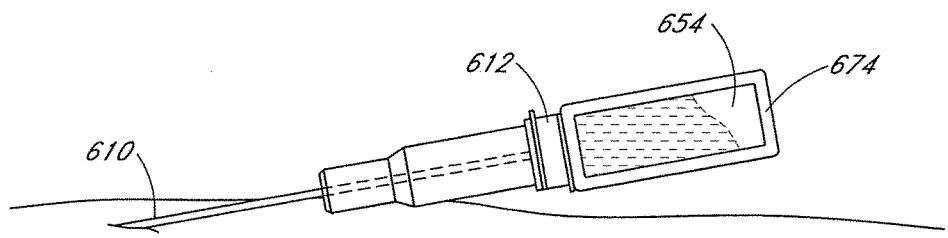
Figure 7C:
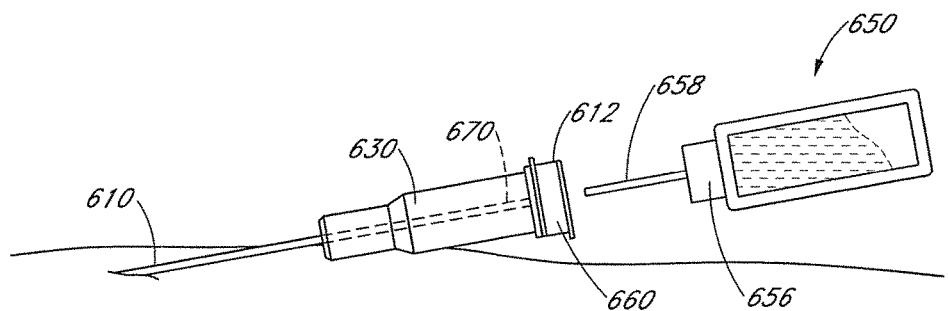

FIGS. 7A-7C shows another vascular access device 598 provided in accordance with further aspects of the present disclosure. In the present embodiment, a catheter hub 630 is provided with a catheter tube 632, which has a needle 610 projecting through the catheter tube 632. The needle 610 is shown attached to a needle hub 612, which is separable from the catheter hub 630 following successful catheterization. Thus, the assembly or device 598 of FIG. 7A is similar to the device of FIG. 6 but with a catheter hub and a catheter tube.

As shown in FIGS. 7A and 7B, a blood collection device 650 comprises a body 652 defining an interior cavity 654 and having a distal projection 656, such as a nose section, having a shaft element 658. The shaft element 658 has a lumen which is in fluid communication with the interior cavity 654 of the blood collection device. The body 652 can be made of a clear or translucent material or have a window to monitor primary blood flashback flowing from the needle 610 into the shaft element 658 and into the interior cavity 654, as further discussed below. The blood collection device 650 is attached to the needle hub 612, such as in a Luer slip or a Luer lock arrangement. With reference to FIG. 7C, which shows the body 652 of the blood collection device 650 separated from the needle hub 612, the distal projection 656 may have a male Luer taper for fitting and engaging with the female Luer on the needle hub 612. A septum 660 may be positioned in the interior cavity of the needle hub 612 at or near the proximal opening of the needle hub 612. When the blood collection device 650 engages the needle hub 612, as shown in FIGS. 7A and 7B, the septum 660 seals around the distal projection 656 of the blood collection device, similar to the device discussed with reference to FIG. 6. Upon disconnection of the blood collection device 650, the septum 660 forms a seal around the slit to prevent leakage out the proximal opening of the needle hub 612. In another example, the needle hub 612 is sized and shaped to enable the septum 660 to be located relatively deeper inside the interior cavity away from the proximal opening so that only the shaft element 658 of the blood collection device 650 projects through the septum 660.

In the used configuration shown in FIGS. 7A and 7B, the shaft element 658 is coupled to the proximal end 670 of the needle 610, which distal tip projects distally of the catheter tube 632. For example, the shaft element 658 connected to the blood collection device 650 may be sized to fit within the lumen of the needle 610. In other examples, the shaft element 658 is larger than the needle 610 and fits over the proximal end of the needle 610, such as receiving the proximal end of the needle 610 in the lumen of the shaft element 658. In still other examples, the shaft element 658 is spaced from the proximal end of the needle 610 and both are distal of the septum located inside the needle hub 612. Alternatively, the proximal end 670 of the needle 610 may be equipped with an elastomeric coupling (not shown) to receive the distal end of the shaft element 658, which is connected to the blood collection device. A separable vent plug 672 is attached to the proximal end of the body 652 of the blood collection device 650, as shown in FIG. 7A. In an alternative embodiment, a gas vent 674, such as a hydrophobic filter, is formed directly to the body 652, as shown in FIG. 7B.

In use, the blood collection device 650 acts as a combination blood stopper and flashback chamber for a typical needle hub of a catheter assembly. For example, with reference to FIGS. 7A and 7B, primary blood flashback or blood flow through the lumen of the needle 610 will be captured by the interior cavity 654 of the body 652 of the blood collection device 650 with zero or minimal blood flashback captured by the needle hub 612 due to the coupling between the needle 610 and the shaft element 658. Once collected, the blood collection device 650 may be removed from the needle hub 612 for disposal or other use, such as to dispense a drop of blood onto a test strip or other blood testing devices.

In another embodiment, the assembly of FIGS. 7A-7C is a catheter assembly and element 612 is a catheter hub, which is shown with the catheter tube penetrated inside a vein of a patient. Element 660 is a needle hub, element 658 is a needle typically provided inside a catheter tube 610. The body 652 is typically a flashback chamber of the needle hub, which in the present embodiment also functions as a blood collection device. Thus, in the alternative embodiment, the needle hub 660/652 is a two-piece hub body that doubles up as a blood collection device.

FIGS. 8A-8D illustrates an embodiment of a blood collection or sampling device 800, which has a hollow compressible body 810 having an interior cavity 814, an actuator 830 located inside the interior cavity, and a gas permeable filter 840 located near a proximal end. The compressible body 810 has a tapered distal portion or tip portion 815, an intermediate portion 820, and a proximal portion 825. As shown, a stem or shaft is located within the interior space of the tip portion 815 so that the blood sampling device is able to retain a reduced amount of blood compared to a tip without the stem. This will allow for reduced blood collection within the blood collection device for certain situations, such as for patients with low blood pressure. The tip portion 815 is tapered to attach to a proximal end 855 of a needle hub 850, such as in a Luer fit. The intermediate portion 820 has a plurality of protruding rings 822 located in an interior thereof to retain the actuator 830 in movable position inside the interior cavity 814. The proximal portion 825 has a stepped surface 827 at the interface with the intermediate portion 820. The stepped surface 827 supports the gas permeable filter 840. The outside surface of the compressible body 810 may incorporate a rough surface to facilitate gripping, twisting, and pulling the compressible body 810. A temporary seal will break or terminate upon twisting. Further, any angle of taper may be incorporated at the tip portion 815, as discussed above, such as any customized tip fitting, to connect the blood collection device to another hub, such as to a needle hub or a catheter hub. In the illustrated embodiment, the rough surface is a plurality of ridges 812 formed on the outside surface of the intermediate portion 820. In other examples, the rough surface can embody a plurality of bumps or divots or combinations thereof. The compressible body 810 is made of a clear or translucent material or can include a window to facilitate viewing into the interior cavity 814 thereof for the presence of blood.

In an example, the actuator 830 includes a distal extending member 832, such as a plunger or a stem, and an activator 834 attached to a proximal end of the distal extending member 832. In the illustrated embodiment, the activator 834 is roughly conical in shape and has an apex 837. As shown, the apex is offset due to the non-symmetrical conical shape of the activator. The activator 834 has an end edge 838 that is angled to a planar surface defined by the gas permeable filter 840. The distal member 832 is connected to the activator 834 at the apex 837 such that the distal member 832 is offset from a central lengthwise axis of the compressible body 810 but parallel to the lengthwise axis. The activator 834 is fitted within the interior cavity 814 of the body 810 and held thereto by interference between the protruding rings 822. In the illustrated embodiment, the end edge 838 is a slanted end edge, which may include serrated or other surface features, such as bumps or roughness features. The activator 834 has a body 839 that incorporates a plurality of diffuser holes 836 that serve as air paths or fluid paths between a distal interior section or chamber 860 located distally of the activator 834 and a proximal interior section or chamber 862 located proximally of the activator 834. Other venting options are contemplated, such as ridges along the outer edge of the activator 834 to permit venting. The activator 834 is sufficiently flexible to be squeezed at the end edge 838 and still be secured to the compressible body 810.

The gas permeable filter 840 is disposed near a proximal end of the compressible body 810. The gas permeable filter 840 can be a vent or filter paper. In the illustrated embodiment, the gas permeable filter 840 is secured to the stepped surface 827 by ultrasonic welding. However, the gas permeable filter 840 can be attached using adhesive, clamping, ultrasonic welding or by interference fit. The permeable filter 840 can be a hydrophobic filter.

Figure 8A:
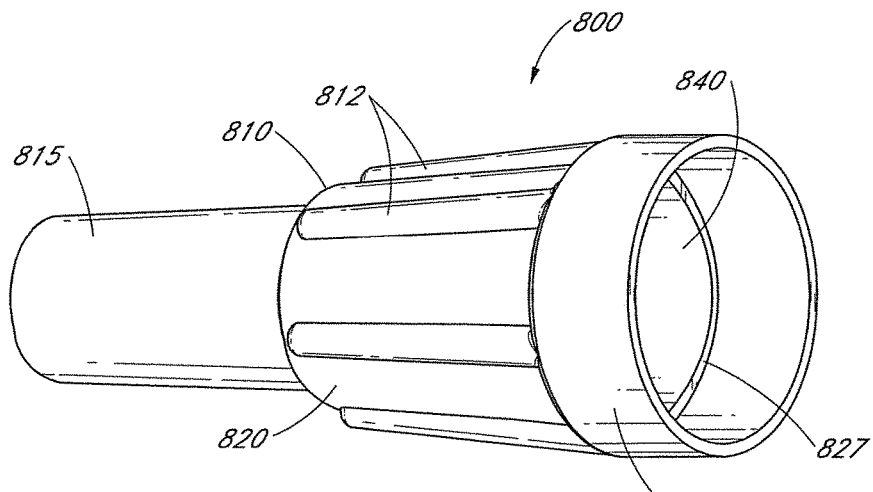
FIG. 8A shows another embodiment of a blood collection device, the blood collection device including a body and an actuator.
Figure 8B:
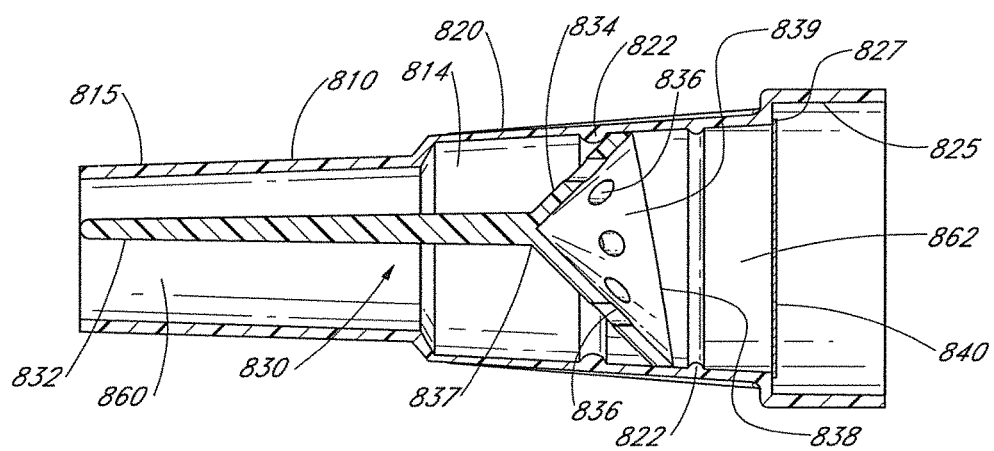
FIG. 8B shows a cross-sectional view of the embodiment of FIG. 8A.
Figure 8C:
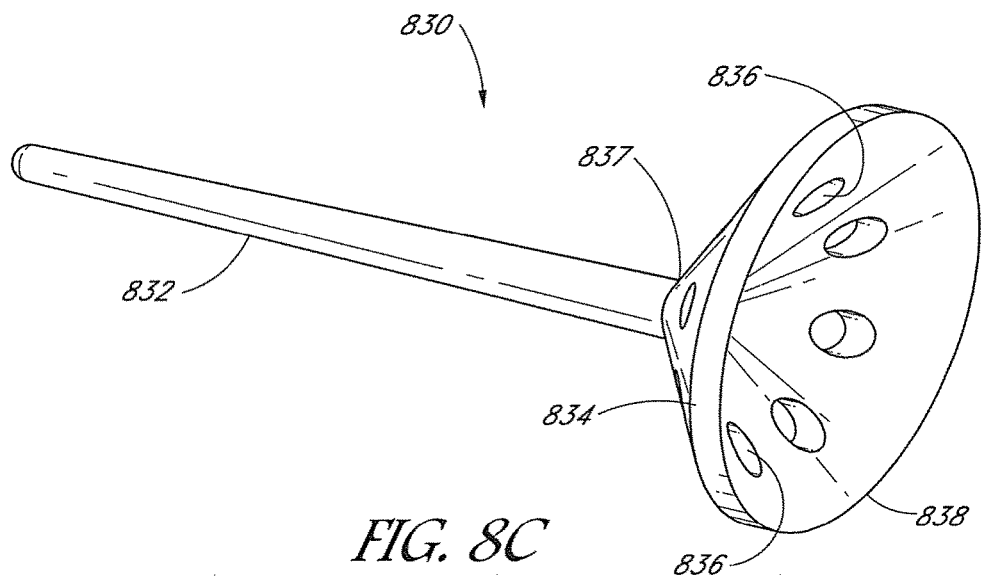
FIG. 8C shows one embodiment of an actuator for use with the blood collection device of FIG. 8A.
Figure 8D:
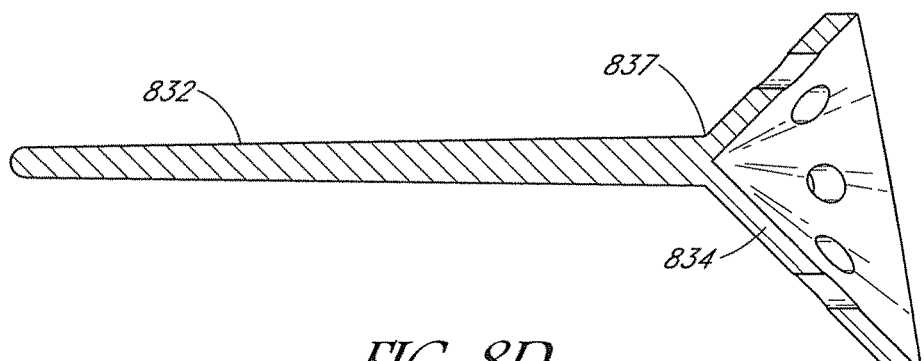
FIG. 8D shows a partial side cross-sectional view of the actuator of FIG. 8C.

FIGS. 8C and 8D are enlarged perspective view and partial cross-sectional side view of the actuator 830 of FIGS. 8A and 8B.

FIGS. 8e and 8F illustrate a catheter assembly 900 including a catheter hub 910, a catheter tube 915 extending distally from the catheter hub 910, a needle assembly 930 having a needle hub attached to a proximal end of the catheter hub 910 and having a needle extending through the catheter tube 915, and a blood sampling device 800 attached to a proximal end of the needle assembly 930. In an example, the blood sampling device 800 is the same as that shown in FIGS. 8A and 8B but can embody any other blood sampling devices described elsewhere herein. The needle assembly 930 includes a needle 932 having a sharp distal tip 933 extending distally through the catheter tube 915 and a proximal portion 934 extending into the interior cavity of the compressible body 810, which has a distal tip portion 815 extending into the proximal opening of the needle hub 936 and around a proximal end 934 of the needle. As the distal member 832 of the actuator 830 is axially offset from the lengthwise axis of the blood sampling device, the proximal end of the needle and the distal member do not mate, abut, or align at their respective axial ends. The needle hub 936 can attach to the catheter hub 910 in a Luer slip or Luer lock arrangement. The blood sampling device 800 preferably engages the needle assembly 930 in a slip fit arrangement. Less preferably, a threaded collar can be provided on the blood sampling device 800 to engage the needle hub 936 in a Luer lock.

A needle guard 950 comprising a proximal wall with a proximal opening for engaging a change in profile on the needle, such as a crimp, and two arms extending distally of the proximal wall is shown positioned inside the catheter hub 910. Upon retraction of the needle, the needle guard closes over the needle tip to cover the needle tip from unintended needle sticks. The catheter may further include a valve having one or more slits and a valve opener to open the valve following successful venipuncture, when an adaptor or a male medical implement is inserted into the catheter hub to advance the valve opener into the valve. Aspects of the needle guard, valve, and valve opener are disclosed in U.S. Pat. Nos. 8,333,735 and 8,591,468, the contents of which are expressly incorporated herein by reference.

The interior cavity of the compressible body 810 retains blood entering through the needle 932 when a successful venipuncture is achieved, known as primary blood flashback. As blood flows through the needle lumen and enters the interior cavity of the tip 815 of the compressible body 810, air or gas is displaced through the diffuser holes 836 and out the gas permeable filter 840. Because the plunger 832 of the actuator 830 is offset from a central axis of the needle assembly, there is no interference between the needle 932 and the distal member 832 when the blood sampling device 800 is installed to the needle assembly 930 and blood flow into the tip 815 simply covers the exterior of the plunger 832, either completely or partially. Blood flashback can fill at least part of the distal interior chamber 860 and possibly some of the proximal cavity chamber 862.

Figure 8G:
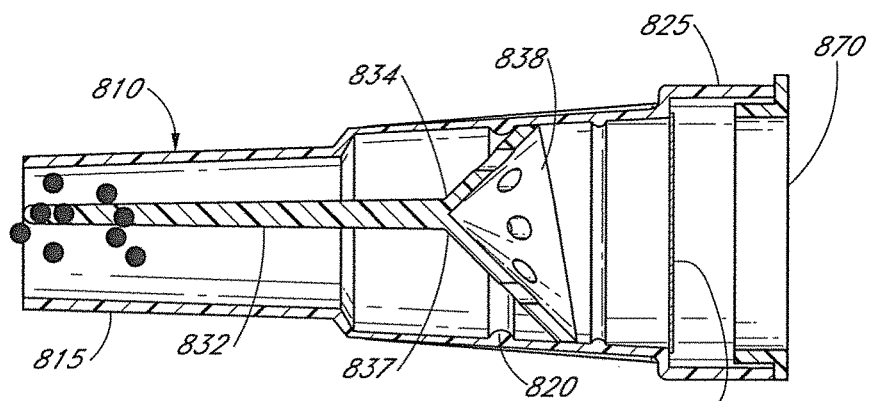
FIG. 8G shows a cross-sectional view of the blood collection device of FIG. 8A in use in a holding state with blood retained.
Figure 8H:
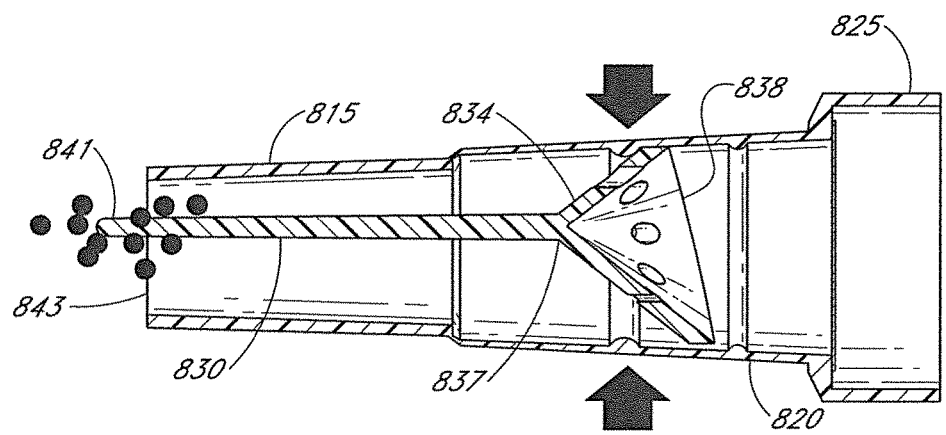
FIG. 8H shows a cross-sectional view of the blood collection device of FIG. 8A in use in a releasing state with blood flowing.

Referring now to FIGS. 8G and 8H, when the needle assembly 930 is retracted from the catheter hub 910, a septum or valve in an interior cavity of the catheter hub 910 can prevent blood from flowing out a proximal opening of the catheter hub. During retraction, the needle guard 950 (FIG. 8F) activates to cover the needle tip to prevent unintended needle sticks. The blood sampling device 800 is then twisted or separated from the needle assembly 930, such as by pulling. Prior to removing the blood sampling device 800 from the needle hub 936 of the needle assembly 930 and allowing blood to flow into the interior cavity of the tip end 815, an optional cap 870 can be installed at the proximal end opening of the blood sampling device 800, such as by frictional or snap fit arrangement with the proximal end of the body 810. The cap 870, which can be similar to the cap of FIG. 6, creates an enclosed headspace at the proximal end of the body 810 to prevent blood from spilling out the distal opening of the tip 815, generating a suction effect similar to covering one end of a filled drinking straw and preventing liquid from draining back out the non-covered end. The cap 870 therefore helps to retain the blood in the blood collection device 800. Even without a cap, blood can coat on the gas permeable filter 840 to create a similar enclosed headspace effect, thus preventing or limiting blood from spilling out the distal opening of the tip 815. To obtain a blood sample, the compressible body 810 can be squeezed at the outer surface of the compressible body 810 at a region close to the end edge 838 of the activator 834, represented by the two arrows shown in FIG. 8H. Squeezing the intermediate portion 820 of the compressible body 810 at or close to the two arrows will also cause the activator 834 located inside to be squeezed. Because the activator 834 is generally cone shape, the squeezing thereof causes the position of the apex 837 to move, such as to the left of FIG. 8H. Movement of the activator 834 at the apex 837 causes the stem 830 to move and its distal tip 841 to protrude forward. In an example, the distal tip 841 protrudes out a planar surface defined by the opening 843 at the tip 815. Movement of the stem 830 disrupts the surface tension of blood at the distal opening 843 of the compressible body 810 thereby allowing the blood to drip out more easily so that a blood sample can be obtained.

As noted, the blood collection devices discussed herein may be used for testing blood collected therein. For a typical medical procedure, a user separates a blood collection device from a needle hub. The size and shape of the Luer tip, shaft element, or stem at the distal end of the blood collection device is such that the Luer tip, shaft element, or stem forms a droplet of blood. A user may then use a marker-type stroke to apply the blood to testing materials or to dispense a droplet for testing. Other application techniques may be used, depending on the requirements of the testing materials. The blood collection device, as with any of the blood collection devices discussed herein, can be made of a material that allows it to be squeezed, forming additional droplets, one at a time. Multiple tests may be performed based on the volume of blood contained in the blood collection device.

Thus, aspects of the present disclosure is understood to include a needle assembly for drawing blood, a blood collection device attached directly or indirectly to the needle hub of the needle assembly and/or to a catheter hub, such as through a Y-site or adaptor connected to a tubing that is connected to the catheter hub. The needle is configured to access the vascular system to draw blood, which then passes to the blood collection device via the needle lumen, which has a tip having a discontinuity opening, an opening with a movable stem, or a shaft element with a lumen. The blood collection device can then be separated from the needle hub, catheter hub, or adaptor and use like a marker to swipe a sample of blood onto a test strip or other test instrument. The blood collection device in the aforementioned embodiments can be incorporated with the needle assembly and is not limited to only the embodiments described. Further, it is understood that the blood collection device is to detect primary flashback as well as dispensing blood droplets for a blood sample. Therefore the choice of material, such as a clear material or translucent material such as a clear polymer, and/or monitoring windows located within the body of the blood collection device can be incorporated in any of the embodiments of the blood collection devices disclosed.

Method of making and method of using the needle assemblies, catheter assemblies, and blood collection devices described herein are contemplated.

Although limited embodiments of the blood collection device assemblies and their components have been specifically described and illustrated herein, many modifications and variations will be apparent to those skilled in the art. Furthermore, it is understood and contemplated that features specifically discussed for one blood collection device embodiment may be adopted for inclusion with another blood collection device embodiment, provided the functions are compatible. For example, a shovel tip may be used around the leading edge of embodiment with a dome with an oculus, replacing the pin or post. Accordingly, it is to be understood that the blood collection device assemblies and their components constructed according to principles of the disclosed device, system, and method may be embodied other than as specifically described herein. The disclosure is also defined in the following claims.

What is claimed is:

1. A needle assembly comprising:
    a needle with a needle tip attached to a needle hub comprising an opening and an interior cavity;
    a blood collection device connected to the needle hub and comprising:
        a frusto-conical shaped tip extending from a body comprising a wall and defining an interior cavity to store blood;
        a gas permeable vent disposed on the wall; and
    wherein the frusto-conical shaped tip of the blood collection device projects into the opening of the needle hub and into the interior cavity of the needle hub to receive blood flashback, and the frusto-conical shaped tip of the blood collection device has an opening comprising a movable stem located within an interior space of the frusto-conical shaped tip of the blood collection device; and
    wherein the needle defines a lengthwise axis and wherein the movable stem is located off the lengthwise axis.

2. The needle assembly of claim 1, wherein the frusto-conical shaped tip of the blood collection device is a Luer tip.

3. The needle assembly of claim 1, further comprising a catheter hub with a catheter tube and wherein the needle extends through the catheter tube.

4. The needle assembly of claim 3, wherein a needle guard is positioned inside an interior cavity of the catheter hub.

5. The needle assembly of claim 1, wherein the movable stem is connected to a non-symmetrical activator having an apex.

6. A method for manufacturing a needle assembly comprising:
    forming a needle hub comprising an opening and an interior cavity and attaching a needle to a distal end of the needle hub and projecting the needle through a catheter hub and a catheter tube;
    forming a blood collection device comprising:
        a frusto-conical shaped tip extending from a body comprising a wall and defining an interior cavity with a storage capacity; and
        a gas permeable vent disposed on the wall;
    projecting the frusto-conical shaped tip into the opening and into the interior cavity of the needle hub so that the interior cavity of the needle hub and the interior cavity of the blood collection device are in fluid communication; and
    wherein the frusto-conical shaped tip comprises an opening comprising a movable stem movable within the interior space of the frusto-conical shaped tip with an activator having an apex and the movable stem is attached to the activator at the apex.

7. The method of claim 6, further comprising projecting a proximal end of the needle into the interior cavity of the needle hub so that the frusto-conical shaped tip of the blood collection device surrounds the proximal end of the needle.

8. The method of claim 6, further comprising placing a needle guard inside an interior cavity of the catheter hub.

9. The method of claim 6, wherein the body of the blood collection device is made from a compressible plastic material.

10. The method of claim 8, further comprising a valve and a valve opener located inside the interior cavity of the catheter hub.

11. A needle assembly comprising:
    a catheter hub having a catheter tube coupled to a needle connected to a needle hub having a needle hub interior cavity, said needle projecting through the catheter hub and the catheter tube;
    a blood collection device connected to the needle hub and comprising:
        a body defining a body interior cavity to store blood; and a tip extending distally from the body into the needle hub interior cavity, the tip having an opening comprising a movable stem located within an interior space of the tip;

wherein the needle defines a lengthwise axis and wherein the movable stem is located off the lengthwise axis.

12. The needle assembly of claim 11, wherein the blood collection device further comprises a gas permeable vent disposed on the body of the blood collection device to vent air from the body interior cavity.

13. The needle assembly of claim 11, wherein the movable stem is connected to a non-symmetrical activator having an apex.

14. The needle assembly of claim 13, wherein the activator has a plurality of diffuser holes to provide air paths of fluid paths between a distal interior section located distally of the activator and a proximal interior section located proximally of the activator.

\* \* \* \* \*

UNITED STATES PATENT AND TRADEMARK OFFICE
CERTIFICATE OF CORRECTION

PATENT NO. : 9,737,252 B2
APPLICATION NO. : 14/576802
DATED : August 22, 2017
INVENTOR(S) : Hui Kuun Teoh et al.

Page 1 of 1

It is certified that error appears in the above-identified patent and that said Letters Patent is hereby corrected as shown below:

In the Specification

In Column 11, Line 36, delete "8e" and insert -- 8E --, therefor.

Signed and Sealed this
Eleventh Day of December, 2018

Andrei Iancu
*Director of the United States Patent and Trademark Office*